United States Patent
Aman et al.

(10) Patent No.: US 9,468,447 B2
(45) Date of Patent: Oct. 18, 2016

(54) LIMITED-USE TOOL SYSTEM AND METHOD OF REPROCESSING

(71) Applicant: Insurgical LLC, Austin, TX (US)

(72) Inventors: Peter M. Aman, Austin, TX (US); Frederick N. Matthews, North Miami, FL (US); Matthew F. Jones, Ft. Worth, TX (US)

(73) Assignee: Insurgical, LLC, Austin, TX (US)

( * ) Notice: Subject to any disclaimer, the term of this patent is extended or adjusted under 35 U.S.C. 154(b) by 538 days.

(21) Appl. No.: 13/917,370

(22) Filed: Jun. 13, 2013

(65) Prior Publication Data

US 2014/0052135 A1    Feb. 20, 2014

Related U.S. Application Data

(60) Provisional application No. 61/682,808, filed on Aug. 14, 2012.

(51) Int. Cl.
    *A61B 17/00*      (2006.01)
    *A61B 17/16*      (2006.01)

(52) U.S. Cl.
    CPC ...... *A61B 17/16* (2013.01); *A61B 2017/00734* (2013.01); *A61B 2090/0803* (2016.02); *A61B 2090/0814* (2016.02)

(58) Field of Classification Search
CPC .............. A61B 2019/4852; A61B 2019/4868; A61B 2019/4815; A61B 17/1626; A61B 17/1628
See application file for complete search history.

(56) References Cited

U.S. PATENT DOCUMENTS

| | | | |
|---|---|---|---|
| 5,400,267 A * | 3/1995 | Denen ................... | A61B 17/00 128/908 |
| 2011/0034910 A1* | 2/2011 | Ross ................ | A61B 17/07207 606/1 |
| 2012/0253328 A1* | 10/2012 | Cunningham ............ | A61L 2/00 606/1 |
| 2015/0209035 A1* | 7/2015 | Zemlok ................ | G01D 18/008 73/1.01 |

* cited by examiner

*Primary Examiner* — Matthew Lawson
(74) *Attorney, Agent, or Firm* — James R. Bell (57) ABSTRACT

A system of limited-use, battery-operated orthopedic power tools, having data collection modules for recording performance characteristics and data analysis modules with algorithms for performing analysis of performance characteristics and providing recommendations for preventative maintenance and repairs.

19 Claims, 6 Drawing Sheets

LIMITED-USE TOOL SYSTEM AND METHOD OF REPROCESSING

RELATED APPLICATION

This application claims the benefit of priority to U.S. Provisional Application No. 61/682,808 filed Aug. 14, 2012.

FIELD OF THE INVENTION

This disclosure relates generally to an invention and method of reprocessing and performing preventative maintenance in the field of powered surgical instruments, methods of use, and more particularly to instruments used in orthopedic procedures for drilling or cutting bone.

BACKGROUND

Important safety and economic factors for any surgical instrument include sterility, cost of acquisition, maintenance, and reliability during use in the surgical suite. Each of these factors can have a significant impact on the cost of medical care for both the patient and the provider.

In recent years, there has been significant focus on the ever increasing cost of medical care. These cost increases have led to skyrocketing insurance premiums, reduced coverage, reduced reimbursements, increased fees for services, severe reductions in services for some patient groups by some providers, and unfortunately an apparent increase in infections and medical mishaps.

In an effort to reduce costs and improve profitability, both service providers and medical device suppliers are continuously looking for ways to streamline procedures, cut time, cost, and risk from their products and services without reducing the quality of the products or services they provide to their customers. One area to benefit from these savings and improvements has been in the orthopedic surgical field the through the use of high precision, battery powered surgical instrumentation. In the late 1960's and early 1970's battery operated drills were bulky, ill-balanced and required multiple batteries to perform some surgeries due to the limited energy storage capacity and poor efficiency of the electric motors.

Since then, manufacturers have attempted to make batteries more efficient with higher energy storage capacity, reduced size, and improved rechargeable lifespans. Likewise, motor housings such as saw and drill bodies have become more ergonomic, balanced, lightweight and energy efficient. As with many standard hand tools having multiple moving components, instrument manufacturers have reduced weight by utilizing lighter materials such as plastic housings, and gears, and put lightening holes in what were previously solid housings. In some cases, standard mountings for attachments have been replaced with modular fittings, allowing for greater interchangeability and component selections. Additionally, manufacturers have attempted to improve electrical components by upgrading them with more modern components wherever possible.

All of these improvements in equipment design have improved efficiencies, costs and quality in some areas while at the same time increasing costs for acquisition, maintenance and increasing risks and patient safety in other ways that were not previously seen or predicted. Often times cost, quality and safety can be inversely proportional to one another. One example of the increased cost and reduced patient safety is seen in the cleaning and maintenance of instruments.

Recent published reports suggest that many of the surgical instruments used in operations were not being cleaned and/or sterilized appropriately in the very hospital facilities that were established and tasked for that purpose. In numerous reports, following cleaning and sterilization, it was noted that upon closer secondary inspection, the inside of small diameter cannulas and intricate mini-components of arthroscopic shavers that are used for many of today's minimally invasive procedures, contained human tissue and bone fragments from previous surgeries. In other cases, modular components of drills and saws such as chucks, drill bits and blades were found to have similar debris or pieces of cleaning brushes and/or bristles embedded in or on them. These investigations have demonstrated that in most cases the instruments were not cleaned according to manufacturer's specifications which has likely lead to many documented cases of serious, multiple, serial infections for subsequent patients. A pilot program conducted by the Centers for Medicare and Medicaid Services (Schaefer et al., 2010; JAMA 2010; 303(22):2273-2279) inspected 1500 outpatient surgery centers and found that 28% had been cited for infectious control deficiencies associated with equipment cleaning and sterilization. The costs to the patients and the hospitals in both expense and liability to deal with these infections can be and has been staggering.

In other cases, critical battery-operated, motorized tools such as drills or bone saws have ceased to function due to dead batteries that no longer maintain their capacity to hold a charge, or due to internal part failure, often attributable to overuse or lack of proper maintenance. The resultant downtime in the operating suite is extremely costly, as the procedure step must be put on hold while replacement or substitute tools are obtained. Wait times may often exceed 20-30 minutes, resulting in additional anesthesia exposure for the patient, additional operating room time (charged to the patient) and potential delays to other procedures where the replacement or substitute equipment had been scheduled for use in a later procedure. Recent estimates (2005) establish the average cost of operating room time to range between $62/min. (range $21.80-$133.12) depending on the procedure. These figures did not include extra resources provided by the hospital for special, non-routine situations which often occur during standard procedures, and did not include the surgeon and anesthesia provider fees, (anesthesia fees are estimated to be $4/min; range $2.20-$6.10). In each case, the hospital or surgical center must then take the equipment out of service, and send it back to the instrument manufacturer or other service provider for service or replacement.

Hospitals and instrument manufactures are continuously attempting to find improved ways to reduce risk associated with infection in general, and more recently, specifically from improperly cleaned instruments. One approach has been to use more disposable, single-use instruments such as drills, saw blades and plastic cannulas. Additionally, many laparoscopic devices such as, surgical staplers and trocars, are designed as single use items that are intended to be immediately disposed of after use. Unfortunately, at today's acquisition costs, the total cost of ownership and benefits are not always clear for high-use battery-operated, motorized instruments such as saws, drills and reamers used in orthopedic procedures and the idea of disposable powered instruments has not been readily embraced.

A recent trend in the medical community is reprocessing of single use medical instruments, by parties other than the original equipment manufacturer, instead of discarding them after use. During reprocessing, the medical instruments are disassembled, cleaned and sterilized. They are then reassembled for future use. However, since the medical instruments reprocessed for further use are specifically designed only for use during a single procedure, the performance of the medical instruments tend to decline after reprocessing, since the components making up the medical instrument are not adapted for multiple uses and will degrade in performance when used beyond their intended life span. For example, reprocessing of the cutting devices on trocars is intended to extend these devices beyond their intended mission life, but often results in duller cutting edges on the blades because neither the materials used nor the reprocessing method can restore the device to the original manufacturing specifications. A greater force, therefore, is needed to make an initial incision, causing more trauma to the patient. In addition, the use of greater force increases the potential for error during the surgical procedure.

Most hospitals and surgery centers buy high-use, reusable motorized, pneumatic, wired or battery operated, orthopedic surgical equipment and are expected to clean, sterilize, and maintain them internally within the hospital. Unfortunately, the technicians hired to perform this work are typically not qualified or trained to perform this work adequately for the many varieties of powered instruments used. Further, manufacturers rarely provide the hospital/client with the training or diagnostic equipment necessary to evaluate or test the equipment themselves. Often times the hospital employees responsible for cleaning and maintenance are not technicians at all, being paid slightly more than minimum wage, working at a fast pace to merely wash, count, reload instruments into their appropriate system trays and flash sterilize them as quickly as possible, in an effort to keep the equipment in rotation in the hospital operating rooms, where higher throughput dictates profitability for the hospital or surgery center.

As a result of high throughput requirements, general maintenance is rarely done and preventative monitoring and maintenance is almost never done on this type of equipment. Hospital budgets for internal maintenance of equipment are generally geared toward higher-end, multi-million dollar capital equipment such as x-ray and radiological equipment. It is generally assumed that it is faster, simpler, and more economical for the hospital to wait for hand-held instruments, such as drills, saws and reamers to fail, then, send them back to the manufacturer for repair or replacement.

Thus it has become apparent that there is a need for an improved system of cost-effective, battery-operated, motorized tools in conjunction with better cleaning and maintenance protocols which can provide the hospital, surgeon, and most importantly, the patient, with a higher degree of safety, efficiency, and cleanliness, while reducing risk and keeping the costs of cleaning, maintenance, and repair as low as possible.

SUMMARY

The present invention recognizes and addresses many of the foregoing limitations and drawbacks of others concerning the need to provide hospitals and surgery centers with an improved, more reliable system of cost-effective, battery-operated, motorized tools in conjunction with better cleaning and maintenance protocols.

In the practice of the present invention, the inventive tooling system utilizes a new concept called limited-use tools (LUT); a significant improvement on the single-use, or disposable instrument. The term "limited-use" as applied to orthopedic surgical tools can mean having a limited useful life, or a restricted lifespan for intended use. Preferably in this context, limited-use is intended to mean the number of surgeries where the useful life of the device ranges from more than 1 use to less than 50 surgeries, and more preferably where the useful life of the device ranges from more than 1 use to less than 30 surgeries, and most preferably where the useful life of the device ranges from more than 1 use to less than 20 surgeries.

In one broad respect, the limited-use tools of this system are in some ways similar to both traditional reusable tools and disposable tools, but with some important changes to the tools, as well as the incorporation of a system for reprocessing the used tool that addresses cleaning, resterilization, routine maintenance and the addition of monitored preventative maintenance protocols to maintain optimal performance characteristics of the tool and modular components and to avoid catastrophic failure of a powered tool when used in surgery.

In another broad respect the inventive limited-use tools comprise low-cost, plastic housings, with changes to the tools such as modular reusable attachments.

In another respect the inventive limited-use tools comprise modular reusable attachments that allow for conversion of a hand tool designed for one purpose to a tool used for an alternative purpose.

In another respect the inventive limited-use tools comprise modular single-use attachments that allow for conversion of a hand tool designed for one purpose to a tool used for an alternative purpose.

In alternative embodiments the limited-use tools utilize single use accessory attachments that work with either modular reusable or modular single-use attachments.

In another broad respect the system of limited-use tools incorporates a reprocessing system to enable the legal use of the tool beyond a single-use limitation.

In yet another broad respect, the system of limited-use tools is a method of reprocessing tools in order to maintain the single-use advantages of guaranteed cleanliness, sterility and performance, combined with optimization of a preventative maintenance program for each component to drive per-use cost of the tool assembly below that of either a single-use or reusable tool while maintaining optimum performance characteristics for each use of the tool.

In still another broad respect, this invention is a method of increasing operational tool efficiencies of battery-operated tools used in multiple surgeries by incorporating preventative maintenance protocols utilizing computerized performance tracking and comparison algorithms.

In yet another broad respect this invention is a method of improving risk factors associated with infection control, and reduction of disease and infection transmission due to lapses in cleaning and infection control associated with routine maintenance of reusable powered surgical instruments.

In another broad respect the invention is a method of processing battery-operated tools used in surgery, to improve the cleanliness of instruments used in multiple surgical procedures and reduce the potential for disease and infection transmission due to lapses in cleaning and infection control procedures between procedures.

In yet another broad respect, the invention is a method of logistical processing of powered tools to improve cleanliness, operational efficiencies, safety, and performance.

In still another broad respect, this invention is a kit, comprising a battery-operated hand tool, modular reusable attachments for the hand tool, disposable single-use accessory attachments, an on-board electronic data collection module (DCM), a means for wired or wireless transmission of electronic data, a computerized component analysis module (CAM), and replacement parts.

In still another broad respect, this invention is a kit, comprising a battery-operated hand tool, modular disposable attachments for the hand tool capable of converting the tool to an alternate purpose tool, disposable single-use accessory attachments, an onboard electronic data collection module, a means for wired or wireless transmission of electronic data, a computerized component analysis module, performance and analysis software algorithms, additional accessory attachments, and modular replacement components.

In still another broad respect, this invention is a system comprising powered hand tools, tool collection and transport containers, protocols for cleaning testing, analyzing, repairing, reprocessing, and re-sterilizing used tools, and returning them to surgical rotation.

In still another broad respect, this invention is a system comprising battery-operated hand tools, modular reusable attachments for the hand tool, disposable single-use accessory attachments, an on-board electronic data collection module, tool and modular component collection and transport containers, protocols for cleaning testing, analyzing, repairing, reprocessing, and re-sterilizing used tools, and returning them to surgical rotation.

In still another broad respect, this invention is a system comprising battery-operated hand tools, modular disposable attachments capable of converting the tool to an alternate purpose tool, disposable single-use accessory attachments, an on-board electronic data collection module, collection and transport containers, a means for wired or wireless transmission of electronic data, a computerized component analysis module, computerized algorithms for comparison and analysis of electronic performance data, protocols for cleaning, testing, analyzing, repairing, reprocessing re-sterilizing used tools, re-kitting the tool system, and returning them to surgical rotation.

Still further, it is to be understood that although this disclosure discusses the invention in terms of battery operated tools, one skilled in the art would fully appreciate that this invention has similar application to any pneumatic, wired or electric wall socket-powered instruments as well.

Still further, it is to be understood that different embodiments, as well as different presently preferred embodiments, of this invention, may include various combinations or configurations of presently disclosed features, elements, or their equivalents (including combinations of features or configurations thereof not expressly shown in the figures or stated in the detailed description).

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

DETAILED DESCRIPTION

Reference will now be made in detail to presently preferred embodiments of the invention, examples of which are fully represented in the accompanying drawings. Such examples are provided by way of an explanation of the invention, not limitation thereof. In fact, it will be apparent to those skilled in the art that various modifications and variations can be made in the present invention, without departing from the spirit and scope thereof. For instance, features illustrated or described as part of one embodiment can be used on another embodiment to yield a still further embodiment. Still further, variations in selection of materials and/or characteristics may be practiced, to satisfy particular desired user criteria. Thus, it is intended that the present invention cover such modifications and variations as come within the scope of the present features and their equivalents.

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

Reprocessing: Reprocessing includes all the steps performed to make a contaminated reusable or single-use device patient ready. The steps may include cleaning, functional testing, repackaging, relabeling, disinfection or sterilization.

Manufacturer means any person who designs, manufactures, fabricates, assembles, or processes a finished device. Manufacturer includes but is not limited to those who perform the functions of contract sterilization, installation, relabeling, remanufacturing, repacking, or specification development, and initial distributors of foreign entities performing these functions as set forth at 21 CFR §820.3.

Remanufacturer means any person who processes, conditions, renovates, repackages, restores, or does any other act to a finished device that significantly changes the finished device's performance or safety specifications, or intended use. As set forth at 21 CFR 820.3.

As disclosed above, the present invention is particularly concerned with limited-use powered surgical hand tools comprising low-cost, plastic housings, with changes to the tools such as modular reusable attachments. The inventive limited-use tools may comprise modular reusable attachments, or alternatively, modular single-use attachments that allow for conversion of a hand tool designed for one purpose to a tool used for an alternative purpose. In addition, the limited-use tools may utilize single use accessory attachments that work with either modular reusable or modular single-use attachments.

Figure 1:
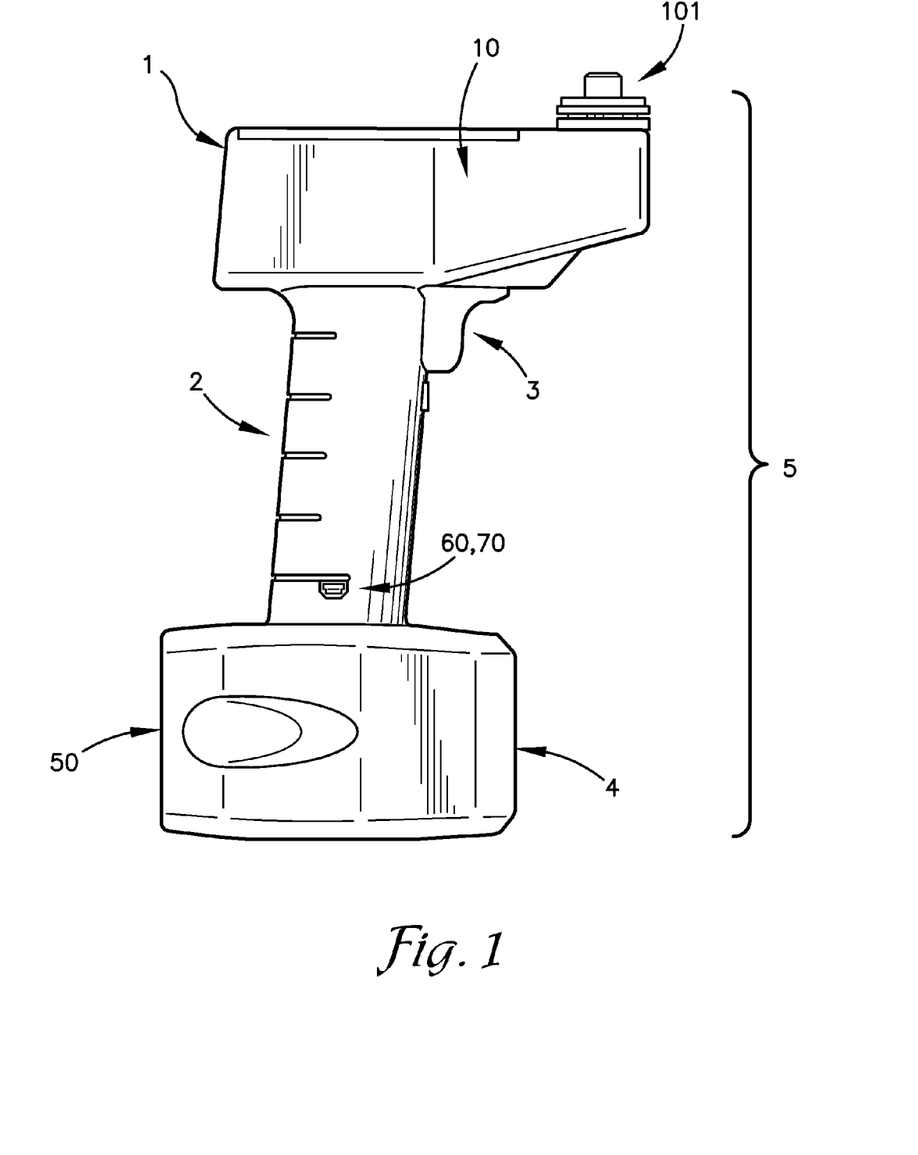
FIG. 1 is a side view of a representative Limited-Use, Battery-operated Hand Saw with a mini USB port (without a protective cover) located in the lower portion of the handle grip, above the battery housing.
Figure 2:
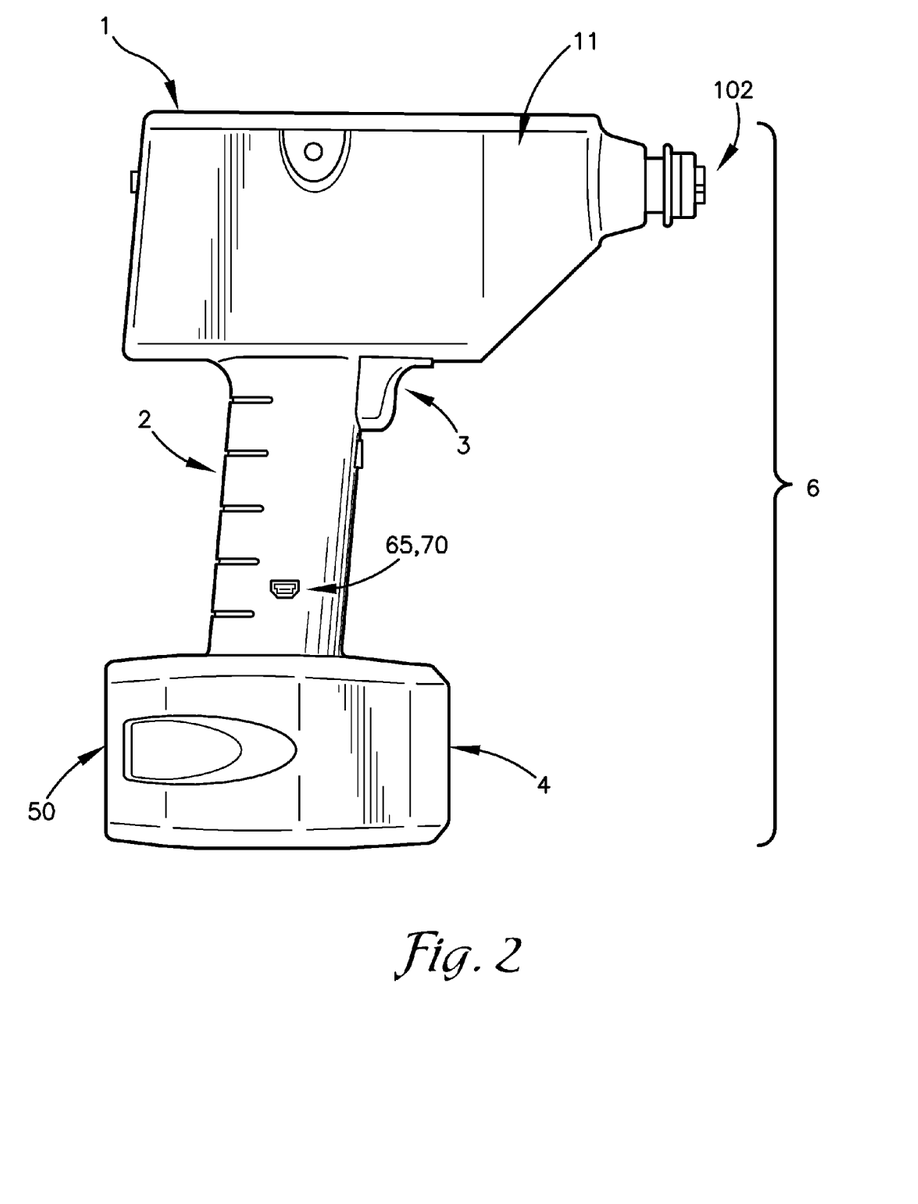
FIG. 2 is a side view of a representative Limited-Use, Battery-operated Drill or Reamer with an alternative wireless data hub (not visible) located internally in the lower portion of the handle grip where a representative wired or USB-type connection might otherwise be placed, above the battery housing.

FIGS. 1 and 2 illustrate representative devices of this invention that has been fully assembled. In FIG. 1, the device motor housing 1 is adapted with a saw attachment module 10 that converts the motor housing into a specific type of powered hand tool; in this case a powered surgical saw. The powered surgical saw device 5 includes a motor housing 1, a saw attachment module 10, having an adaptor hub 101 capable of receiving disposable saw blades (not shown), an ergonomic pistol grip type handle 2, a trigger or start/stop switch 3, a battery housing 4 in the inferior (lower) portion of the pistol grip housing; a rechargeable battery 50, a data transfer hub 60, which could be wired using USB, IEEE 1394, SATA, Ethernet or any other wired interface, connected to a data collection module 70, DCM (not shown), internally located within the ergonomic pistol grip handle 2. The DCM 70 (not shown) would include a controller/processor, on board flash and/or EEPROM memory, and a communications interface. The DCM may be powered either by the LUT rechargeable battery system or a unique, small form-factor battery system.

It should be understood that the saw attachment module 10 of the inventive tool may also be a modular attachment which is designed to be removed by the operating surgeon or surgical technician and replaced with an alternative modular component. The alternate modular component need not necessarily have the same function as the original saw attachment modular, but may in fact convert the tool to perform an entirely new function.

In FIG. 2, the device motor housing assembly 1 is adapted with a drill/reamer attachment module 11 that converts the motor housing into another specific type of powered hand tool; in this case a powered drill or reamer 6. The powered drill or reamer device 6 includes a motor housing assembly 1, a drill/reamer attachment module 11, having a drill/reamer adaptor hub 102 capable of receiving various common fittings such as Jacob chucks, Hudson and Zimmer fittings (not shown) or, alternatively custom tool holding adaptors capable of securely holding disposable or reusable rotating tools such as drills and reamers (not shown), an ergonomic pistol grip type handle 2, a trigger or start/stop switch 3, a battery housing 4 in the inferior portion of the pistol grip housing; a rechargeable battery 50, an alternative wireless data transfer device 65 (not shown) (which may be Bluetooth, Zigbee, IEEE 802.11, ANT, IrDA or other short-range wireless interface), located inside the ergonomic pistol grip handle and connected to a data collection module 70, DCM (not shown), also internally located within the pistol grip handle 2.

It should be understood that the drill/reamer attachment module 11 of the inventive tool may also be a modular attachment which is designed to be removed by the operating surgeon or surgical technician and replaced with an alternative modular component. Said alternate modular component need not necessarily have the same function as the original drill/reamer attachment, but may in fact convert the tool to perform an entirely new function.

Figure 3:
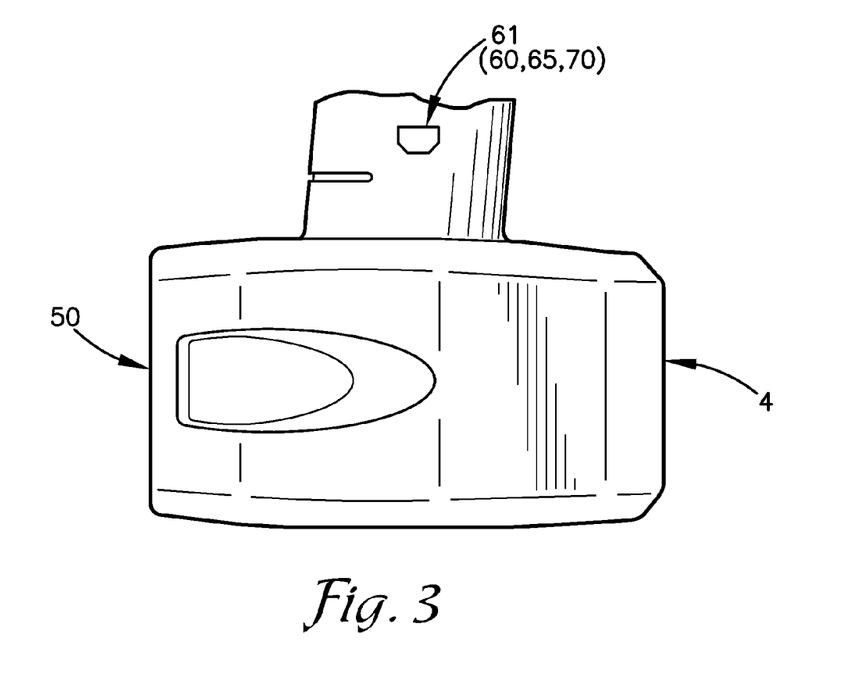
FIG. 3 is a close-up, representative detail view of the lower portion of the tool grip and battery housing, demonstrating the relative location of a data transfer port with a protective cover in place; or alternatively, the relative location of a wireless data transfer hub, (not necessarily visible on the outside of the housing)

FIG. 3 illustrates a detail view of the inferior portion of the pistol grip handle 2 showing the battery housing 4, the rechargeable battery 50 and a representative location of the external wired data transfer hub using USB, IEEE 1394, SATA, Ethernet or any other wired data transfer hub 60 (not shown), with a protective cover, 61, (used only with the wired data transfer hub) covering the external wired data transfer hub to protect it from damage or debris collection when in use. Alternatively, one skilled in the art would understand that a wireless data transfer device 65 such as BLUETOOTH®, Zigbee, IEEE 802.11, ANT, IrDA or other short-range wireless interface (not shown) or a similar technology could be substituted for a wired data transfer hub and be placed anywhere in the device. For illustrative purposes, it is implied that a wireless device could be represented within the pistol grip handle 2, in the same relative location as the wired data transfer hub 60. It is also understood that either the wired data transfer hub 60 or the wireless data transfer device 65 are connected to the Data Collection Module 70, located internally within the pistol grip handle.

Figure 4:
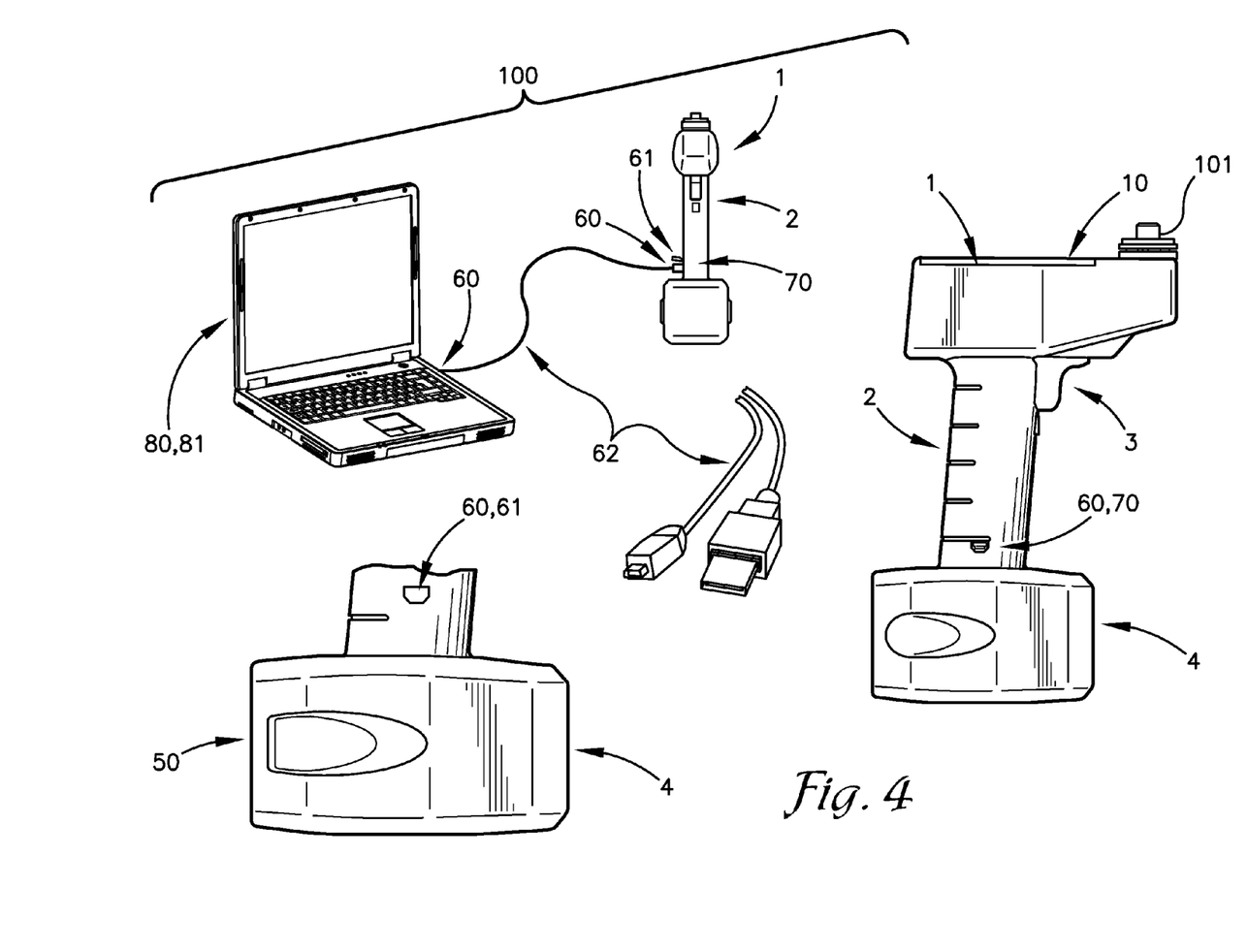
FIG. 4 is a representative view of a wired version of the Limited-Use Tool System with a data transfer interface to the Component Analysis Module.

FIG. 4 illustrates a representative view of the Limited-Use Tool (LUT) System 100 with a wired version of data transfer interface to the Component Analysis Module. The Component Analysis Module would reside on a computing system comprising a processor, both volatile and non-volatile memory, and a standard software operating system such as Windows, Linux or Apple OS. As illustrated, a representative example of the wired data transfer version of the LUT system 100 comprises a device motor housing 1, having a modular attachment (such as a saw attachment module 10 (shown), or drill/reamer attachment module 11, (not shown)), a handle 2, with a start/stop trigger switch 3, an internal Data Collection Module 70 (not shown), an external wired data transfer hub 60, a data transfer connection wire 62, such as a mini USB connection, a battery housing 4, a rechargeable battery 50, and a computer processing system defined as a Computer Analysis Module (CAM) 80 with data storage memory, also comprising analysis software algorithms 81 for collection, manipulation, calculation and analysis of data received from the tool(s) and database stored in the CAM memory.

Figure 5:
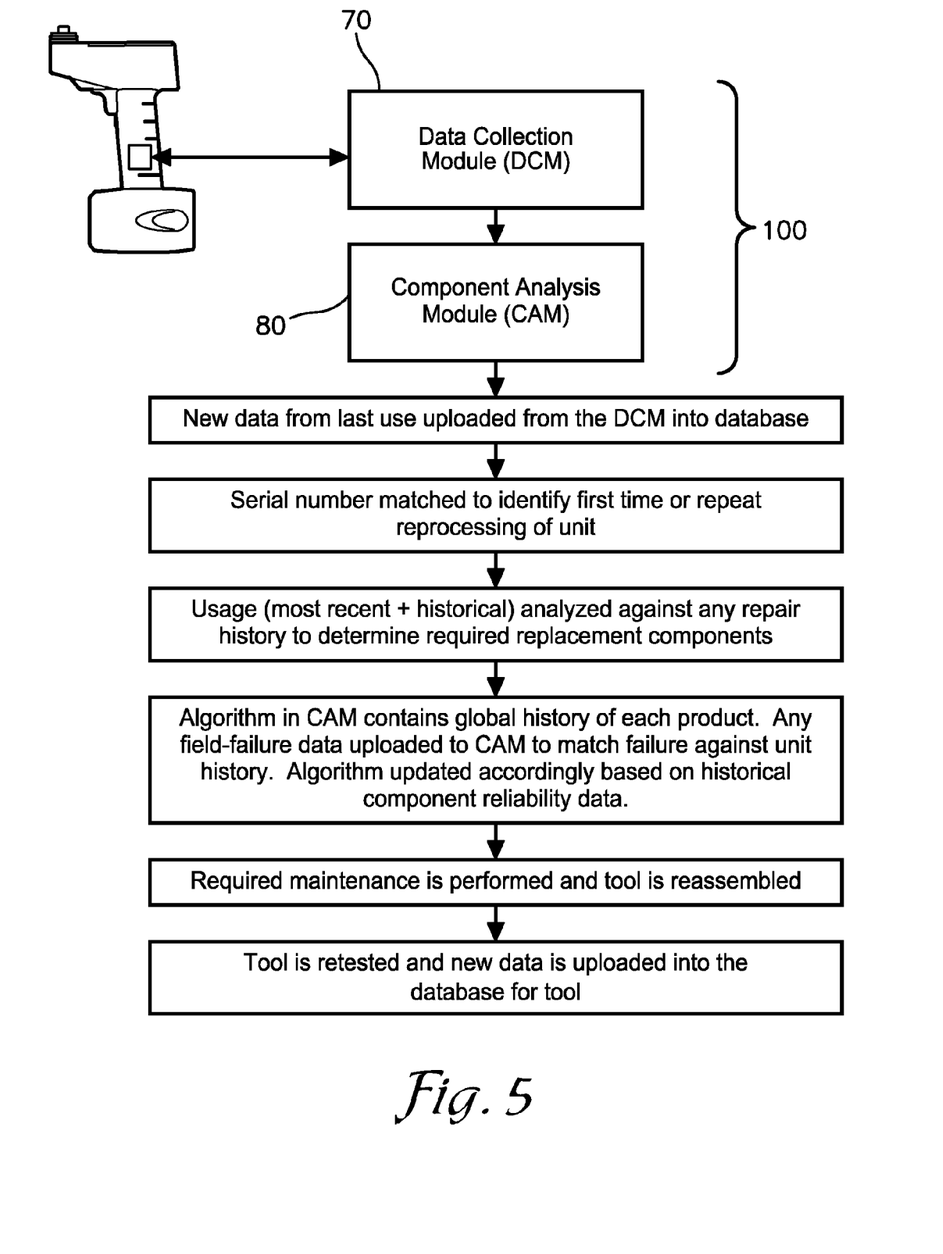
FIG. 5 is a representative illustration of the Data Collection Module's transfer of data to the Component Analysis Module and analysis flow chart.

FIG. 5 is a high level representative illustration of the Limited-Use Tool (LUT) System 100 transfer of data from the Data Collection Module 70 in a representative tool to the Component Analysis Module 80 and an analysis flow chart. Key features of these limited-use tools include; an on-board electronic Data Collection Module (DCM) 70 capable of collecting and storing performance data from sensors in the tools and to provide the following minimum functions: (1) Identify each unique tool (e.g., serial number); (2) capture performance data from internal tool sensors such as: (a) how many hours the tool has operated; (b) battery operating parameters, (c) any "over-use" conditions that may have occurred (according to operating specs), such as: (i) operating temperature peaks, (ii) torque load peaks, (iii) any other critical operating data, (iv) enable an operating time limiter (limiting time of tool use).

Once the tool is collected, returned to the reprocessing facility, cleaned and decontaminated, the collected data stored in the DCM 70 is then transmitted by either wired 60, 62 or wireless 65 interface (not shown) from the DCM 70 to the Component Analysis Module CAM 80 where new data from the last use is uploaded into the database. The serial number is matched to determine whether it is a first time through or a repeat reprocessing of the unit. Following this step the tool usage (most recent+historical) is analyzed using unique system algorithms 81 and compared against any repair history or established manufacturing standards to determine if there is a need for required replacement components, or simple routine maintenance. The algorithms 81 in CAM 80 compare the global history of each product component with any field-failure data uploaded to the CAM 80 to match failure against unit history while comparing the results to the established manufacturing standards recommended for each component. The algorithms can then generate codes or instructions to the technician indicating the recommended maintenance to be performed. The algorithm database is then updated accordingly based upon results of the interim analysis of the component reliability data and most recent use data.

Based on the data analysis and recommendations provided by the algorithm analysis, the technician would then perform the required internal maintenance, replacements, and cleaning before reassembly of the tool. The tool would then be retested by re-connecting it to the CAM 80 to verify that the tool is once again operating within expected parameters. The CAM 80 would be updated with the date, the newest operational performance characteristics, repair information necessary to complete the preventative maintenance log for the tool, such as replacement parts, serial numbers, etc.

Once all of the repairs and maintenance have been performed correctly and the tool is operating as expected, the technician performs a final external cleaning operation to remove any residual external oil or foreign debris before sending the tool on to the next step of the reprocessing protocol for clean packaging and re-sterilization.

Figure 6:
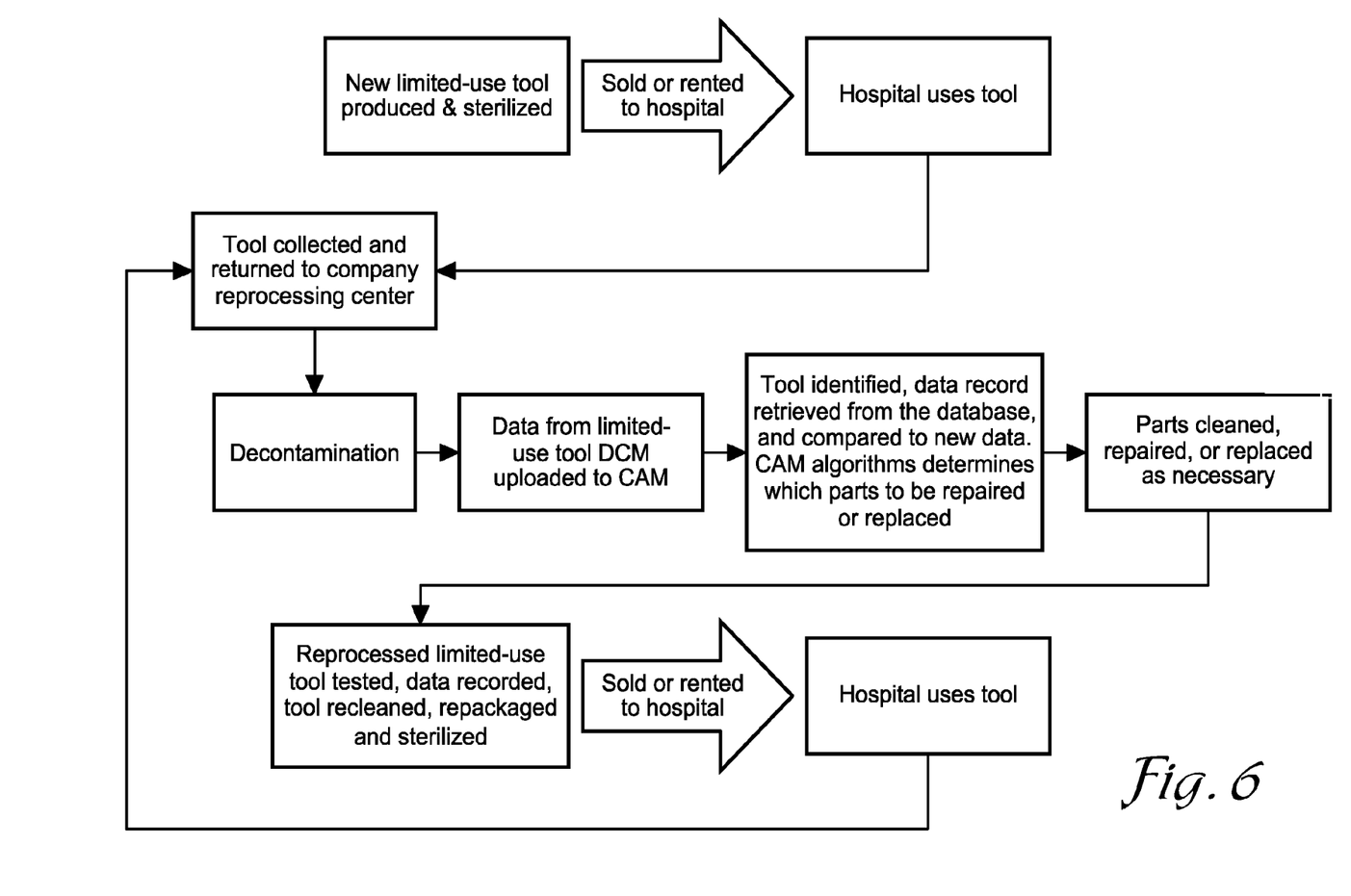
FIG. 6 is a representative flow chart illustrating the logistical processing steps for the inventive system.

FIG. 6 is a representative flow chart illustrating the overall processing steps for the inventive limited-use tool system. An additional key aspect of the inventive system of limited-use tools (LUT) incorporates a preventative maintenance reprocessing system to enable use of the tool beyond a single-use compliant with the requirements of 21 CFR §§807, 814 and 820.

As shown in the flow chart of FIG. 6, a fully sterile and packaged Limited-Use Tool, Tool Kit, Tooling System or Custom Configured LUT with both reusable and disposable components and accessories, may be sold or rented to a hospital or surgical center where it is available for use in a specific procedure. Following the procedure, the tool(s) and reusable components are collected and returned to a company reprocessing center, preferably in standardized transport containers designed to hold and protect the tools and their various modular components from any subsequent damage or mishandling when in transit.

Upon receipt at the company reprocessing center, the tools are removed from the transit containers, and decontaminated. Following decontamination, the tools are linked to the CAM and the operational data from the tool is uploaded from the tool DCM to the system CAM. The system CAM can then identify the tool, retrieve its unique data history from the stored database and compare the new data with the historical data and established manufacturing standards. The unique system algorithm will then analyze the data, compare to predetermined benchmarks for operational performance and provide guidelines to the technician for recommended maintenance and repairs to maintain the tool at optimal performance parameters. The interim data would then be stored in the database as a component of the tool's historical data.

Upon completion of maintenance and repairs, the reprocessed tool is again linked to the CAM to establish a new baseline for the tool's operational performance. The new data is again recorded for that tool in the database. The newly refurbished tool is then sent through a final cleaning and repackaging process before being re-sterilized and returned to available rental inventory, or the customer.

As noted previously, it is another object of this invention to provide an improved maintenance and reprocessing system for powered surgical tools. The essential components of the reprocessing system are: (1) a process or protocol for the routine collection and transfer of used, or non-sterile tools from the hospital or surgical center to a designated reprocessing facility outside of the hospital or surgery center. The system may include standardized containers designed to hold and protect the tools and their various components from any subsequent damage or mishandling while in transit; (2) facilitating the transfer of tools to a designated reprocessing facility capable of receiving non-sterile, contaminated tools, post-surgery. These facilities have the extended ability to clean, inspect, disassemble, perform preventative maintenance evaluations, repair, reassembly, testing, recording of new performance characteristics, repackaging, and optionally, re-sterilization of each tool via ethylene oxide (ETO), Sterrad, gamma irradiation, E-Beam, or a comparable method; (3) facilitating the return of the refurbished tools to the customer.

It is another object of this invention to be able to perform preventative maintenance, versus simple post-hock failure analysis and repair as is normally done with standard, high cost, battery-operated reusable tools found in hospitals today. An essential component of this system is the ability to download key information stored in the data collection module (DCM) that tracks critical components and functions of the tool to a data collection repository or component analysis module (CAM) utilizing software that compares the uploaded data to historical component data and/or predetermined preventative maintenance parameters using specially designed algorithms.

The data from each tool DCM would be uploaded (via wired or wireless I/F) to a Component Analysis Module (CAM) containing the software algorithms to analyze each of the monitored components in the tool. The CAM registers or logs in and identifies each unique tool, retrieves the stored data from the tool's DCM, compares and analyzes the data against the stored data from the previously stored data for that tool and utilizing the CAM algorithms, comparing the test data to optimal design performance characteristics recommended by the manufacturer, and makes recommendations to the technician which components should be cleaned and reused, repaired or replaced with new parts, as well as creates a record of performance for each component. Once known, the technician makes repairs or upgrades as needed, to bring the tool back up to optimal performance characteristics or manufacturing specifications.

Some components may only be used once, by design, whereas others may be used for as many as 50 or more procedures. Reprocessing limits for each component are determined by the confidence level in each component, based on design parameters and manufacturer recommendations to have a high degree of confidence it will not fail during the next time in-use. These confidence levels are utilized to create the algorithms used in the CAM.

Based on the historical data and CAM recommendations resulting from the algorithm analysis, each tool and or component is disassembled as needed, cleaned, components repaired or replaced and reassembled, returning the tool and or the modular components back to its original, or substantially equivalent original specification.

Once repairs and reassembly are completed, the equipment is re-tested to confirm optimal performance. Each tool is subsequently reconnected to the CAM for verification testing and recordation of its updated performance specification for the historical tool record. Data is then stored for future use. All data is maintained and traceable to support any future FDA or legal inquiry.

Once testing and verification are completed, the reprocessing protocol moves each tool and or component onto a final cleaning and repackaging step. At this stage, the tools are cleaned or any residual materials, oils or cleaning solvents before being repackaged in sterile OR compatible packaging.

Finally, the tools are processed for re-sterilization with ETO, gamma radiation, STERRAD, E-Beam, or other comparable sterilization method before being returned to available stock, or returned to the client hospital or surgical center.

In the preceding description, the devices and methods are described with reference to exemplary embodiments thereof. Various modifications and changes may be made thereto without departing from the broader spirit and scope of the disclosure.

We claim:

1. A system comprising:
an orthopedic hand tool with reusable modular attachments and an on-board electronic data collection module to monitor and record operational performance characteristics of the tool and the reusable modular attachments, wherein an external component analysis module receives operational performance characteristics data and
wherein the external component analysis module resides on a computing system comprising: (1) a central processing unit, (2) a memory device, and (3) an operating system wherein the received data is analyzed and compared to optimal performance characteristics and available historical data assigned to the orthopedic hand tool using algorithms to make recommendations for preventative maintenance and or repairs in order to maintain or restore the performance of said orthopedic hand tool to optimal operational parameters.

2. The system of claim 1, wherein the orthopedic hand tool is battery operated.

3. The system of claim 1, wherein the orthopedic hand tool and reusable modular attachments provide a useful life in the range of more than 1 surgery to about 50 surgeries.

4. The system of claim 1, wherein the orthopedic hand tool and reusable modular attachments provide a useful life in the range of from more than 1 surgery to about 30 surgeries.

5. The system of claim 1, wherein the orthopedic hand tool and reusable modular attachments provide a useful life in the range of from more than 1 surgery to about 20 surgeries.

6. The system of claim 1, wherein the on-board electronic data collection module transfers operational performance characteristics data to the component analysis module using a serial communication architecture.

7. The system of claim 1, wherein the on-board electronic data collection module transfers operational performance characteristics data to the component analysis module using a wireless communications protocol.

8. The system of claim 1, wherein the on-board electronic data collection module transfers the operational performance characteristics data to a component analysis module using a wireless communications protocol.

9. The system of claim 8, wherein the wireless communications protocol is compliant with at least one of: (1) Bluetooth, (2) Zigbee, (3) IEEE 802.11, (4) ANT, and (5) IrDA.

10. The system of claim 1, wherein the data collection module further comprises: (1) a central processing unit, (2) memory hardware, and (3) a communications interface.

11. The system of claim 1, wherein the orthopedic hand tool has reusable modular attachments comprising, a saw, a drill, and a reamer.

12. The system of claim 1, wherein the reusable modular attachments convert the orthopedic hand tool designated for one purpose to an alternative purpose.

13. The system of claim 1, further comprising an embedded preventative maintenance function with a data collection module for recording the performance characteristics of the orthopedic hand tool with modular components and capable of transmitting the recorded performance characteristics to a computerized component analysis module with software algorithms for analysis of the performance characteristics and maintenance recommendation generation.

14. An orthopedic hand tool comprising:
a motor housing;
a power supply;
modular reusable attachments;
a data collection module for monitoring and storing performance characteristics of the motor and modular reusable attachments;
wherein an external component analysis module receives operational performance characteristics data; and
wherein the external component analysis module resides on a computing system comprising: (1) a central processing unit, (2) a memory device, and (3) an operating system wherein the data is analyzed and compared to optimal performance characteristics and available historical data assigned to the orthopedic hand tool using algorithms to make recommendations for preventative maintenance and or repairs in order to maintain or restore the performance of said orthopedic hand tool to optimal operational parameters.

15. A surgical hand tool kit comprising:
a motorized hand tool;
a detachable battery power supply;
at least one modular attachment for performing surgical procedures;
a data collection module for capturing and storing performance characteristics of the motor and modular reusable attachments;
wherein an external component analysis module receives operational performance characteristics data; and
wherein the data is analyzed and compared to optimal performance characteristics and available historical data assigned to the orthopedic hand tool using algorithms to make recommendations for preventative maintenance and or repairs in order to maintain or restore the performance of said orthopedic hand tool to optimal operational parameters.

16. An orthopedic surgery kit comprising:
a battery-operated hand tool;
a plurality of modular attachments;
an electronic data collection module housed within the hand tool for storing a series of performance parameters for the battery, the hand tool and the plurality of modular attachments;
data transmission hardware;
a component analysis module for receiving and analyzing the transmitted data; and
wherein the data is analyzed and compared to optimal performance characteristics and available historical data assigned to the hand tool using algorithms to make recommendations for preventative maintenance and or repairs in order to maintain or restore the performance of said orthopedic hand tool to optimal operational parameters.

17. A battery powered surgical tool that can be refurbished to optimal performance following use, the surgical tool comprising:
- a battery-operated hand tool;
- at least one modular attachment;
- an electronic data collection module housed within the hand tool for storing a series of performance parameters for the battery, the hand tool and the plurality of modular attachments;
- data transmission hardware disposed within the hand tool; and
- a component analysis module for receiving and analyzing through the use of algorithms, the transmitted data, wherein based upon the component analysis module recommendations resulting from the algorithm analysis, the battery operated hand tool, battery and modular attachment is disassembled as needed, cleaned, repaired or replaced and reassembled thereby returning the tool, battery and attachment to original, or substantially equivalent original specification.

18. A battery powered surgical tool that can be refurbished to optimal performance following use, the surgical tool comprising:
- a battery-operated hand tool;
- at least one modular attachment;
- an electronic data collection module housed within the hand tool for storing a series of performance parameters for the battery, the hand tool and the plurality of modular attachments;
- data transmission hardware disposed within the hand tool; and
- a component analysis module for receiving and statistically analyzing through the use of algorithms, the transmitted data, wherein based upon the component analysis module recommendations resulting from the algorithm analysis, the battery operated hand tool, battery and modular attachment is disassembled as needed, cleaned, repaired or replaced and reassembled thereby returning the tool, battery and attachment to original, or substantially equivalent original specification.

19. The battery powered surgical tool of claim 18, wherein the surgical tool is reassembled.

* * * * *